(12) United States Patent
Meese

(10) Patent No.: US 6,809,214 B2
(45) Date of Patent: Oct. 26, 2004

(54) SHORTENED SYNTHESIS OF 3,3-DIARYLPROPYLAMINE DERIVATIVES

(75) Inventor: Claus O. Meese, Monheim (DE)

(73) Assignee: Schwartz Pharma AG (DE)

( * ) Notice: Subject to any disclaimer, the term of this patent is extended or adjusted under 35 U.S.C. 154(b) by 18 days.

(21) Appl. No.: 10/297,778

(22) PCT Filed: Jun. 11, 2001

(86) PCT No.: PCT/EP01/06577
§ 371 (c)(1),
(2), (4) Date: Dec. 9, 2002

(87) PCT Pub. No.: WO01/96279
PCT Pub. Date: Dec. 20, 2001

(65) Prior Publication Data
US 2003/0212292 A1 Nov. 13, 2003

(30) Foreign Application Priority Data
Jun. 14, 2000 (DE) .......................................... 100 28 443

(51) Int. Cl.$^7$ ....................... C07C 229/00; C07D 309/00
(52) U.S. Cl. ........................... 560/36; 562/441; 549/273
(58) Field of Search ........................... 560/36; 562/441; 549/273

(56) References Cited

U.S. PATENT DOCUMENTS 5,559,269 A * 9/1996 Johansson et al. .......... 564/443

FOREIGN PATENT DOCUMENTS

| EP | 0325571 A1 | * | 1/1989 |
| EP | 0957073 A1 | * | 5/1998 |
| WO | WO 98/43942 | * | 10/1998 |

OTHER PUBLICATIONS

Speranza, Uncatalyzed Reaction of Phenols and Naphthols with Methyl Cinnamates. A Simple Synthesis of 4–Arylchroman–2–ones and 1–Arylbenzo[f]chroman–3–ones, Aug. 1997, pp. 931–936.*

* cited by examiner

Primary Examiner—Paul J. Killos
(74) Attorney, Agent, or Firm—Peter F. Corless; Christine C. O'Day; Edwards & Angell, LLP

(57) ABSTRACT

The invention relates to a method for producing derivatives of 3,3-diarylpropylamines of general formula (I) and sterically highly pure, stable intermediate products, and to their use for producing pharmaceutical compositions.

14 Claims, No Drawings

SHORTENED SYNTHESIS OF 3,3-DIARYLPROPYLAMINE DERIVATIVES

This patent application claims the benefit of priority under 35 U.S.C. §119 of PCT patent application Ser. No. PCT/EP01/06577, filed Jun. 11, 2001 and German Patent Application DE 100 28 443.4, filed on Jun. 14, 2000, both of which are incorporated herein in their entirety by reference.

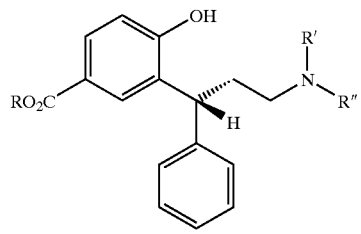

Formula I

In particular, the invention relates to a process for the production of a compound of formula II

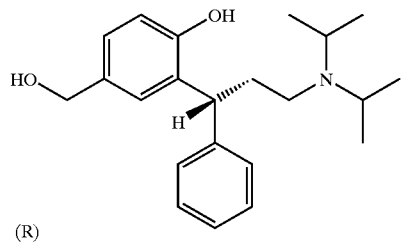

Formula II and to pharmaceutically valuable intermediates.

From U.S. Pat. No. 5,559,269 a process for the production of a compound of formula II is known. This process comprises 11 process steps before this compound is obtained. The R enantiomer is obtained in this process by resolution of racemates with a chiral acid in process step 5.

From PCT/EP99/03212=WO 99/58478, a process for the production of a compound of formula II is known, which comprises 12 process steps. According to this, the resolution of racemates takes place using a chiral base in process step 2.

Both processes have the disadvantages that, owing to the large number of process steps involved in the synthesis, they are very complex and lead to an unsatisfactory yield.

The object of the present invention is therefore to avoid the above-mentioned disadvantages.

Surprisingly, this object has been achieved in that a process is provided which comprises only 6 process steps, in which the necessary resolution of racemates takes place as early as step 1 of the process and which has the features mentioned in the claims.

To produce 3,3-diarylpropylamines of the general formula I mentioned above, 4-hydroxybenzoic acid or its low alkyl esters (PHB esters; para-hydroxybenzoates), preferably its methyl esters according to formula 1, are used as starting compounds,

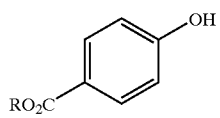

Formula 1 which are reacted with cinnamic acid to form a compound of the general formula 2

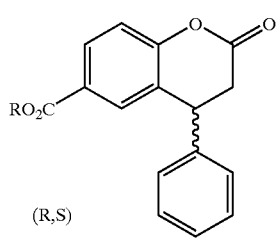

Formula 2 wherein

R has the meaning of hydrogen, straight-chained or branched $C_1$–$C_6$ alkyl, preferably methyl or isopropyl. By conducting the reaction in a particular way, starting from 4-hydroxybenzoates, the free, crystalline acid according to formula 2a can be obtained directly as a reaction product according to the process.

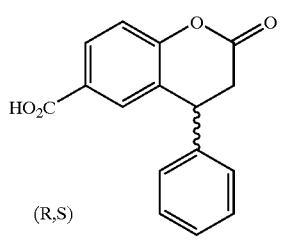

Formula 2a

The reaction takes place at elevated temperatures and with catalysis. The preferred solvent is acetic acid. Protonic acids such as sulfuric acid have proved suitable as the catalyst and favourable temperatures are between 50° C. and 117° C., preferably 100° C. The compounds of formula 2a are obtained under the above reaction conditions as crystalline solids in a yield of about 70–78% and in good purity (>90%). The purity is further increased by recrystallisation, e.g. from 2-butanone, acetic acid or N-methylpyrrolidin-2-one.

Crystalline salts are obtained with inorganic or organic bases. Chiral organic bases yield diastereomeric salts, in each of which one enantiomer is noticeably concentrated. If the tertiary, chiral amine cinchonidine is used, the crystalline salt according to formula 2b is obtained in 90% purity, in which the R enantiomer predominates as the acid component at over 95%. By further recrystallisation, an increased optical purity of 99% e.e. is obtainable.

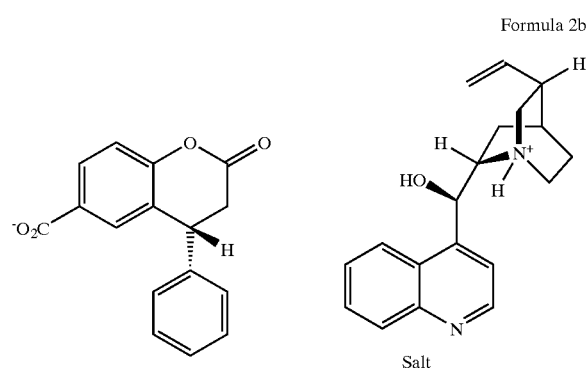

Formula 2b

Salts in which the base component is formed from other chiral amines, on the other hand, do not lead to any significant optical concentration.

The free acid according to the compound of formula 3 is isolated by acidification of aqueous solutions or suspensions and extraction with a suitable solvent. According to the invention, ethyl acetate is preferably used.

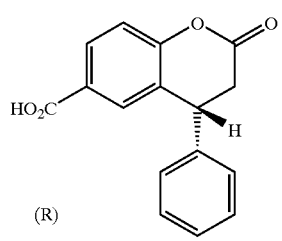

Formula 3

(R)

The pure compound of formula 3 is stable and crystalline. Further recrystallisation leads to high chemical and optical purity of over 99%.

The dextrorotatory compound of formula 3 is converted, after activation, to esters of the general formula 4, in which R has the meaning of straight-chained or branched $C_1$–$C_6$ alkyl, preferably methyl or isopropyl.

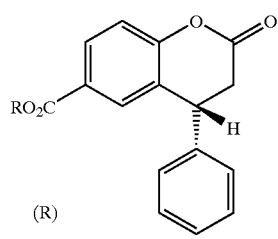

Formula 4

(R)

According to the invention, the reaction is performed with thionyl chloride or oxalyl chloride via the intermediate step of an acid chloride, which is followed by ester formation with alcohols of the R—OH type, in which R has the meaning of linear or branched-chain $C_1$–$C_6$ alkyl, preferably methyl or isopropyl, in the presence of suitable bases.

The esters obtained, of the lactone type, are in the form of stable, colourless, crystalline substances.

Another aspect of the invention is the targeted utilisation of differing reactivity of the carboxyl groups of the lactone ring and of the aromatic ester towards hydride reagents.

Thus, when these reagents act on compounds of formula 4, preferably diisobutylaluminium hydride or lithium tri-tert.-butoxyaluminium hydride, reduction of the lactone to the lactols of formula 5 (e.g. R=methyl or isopropyl) occurs almost exclusively.

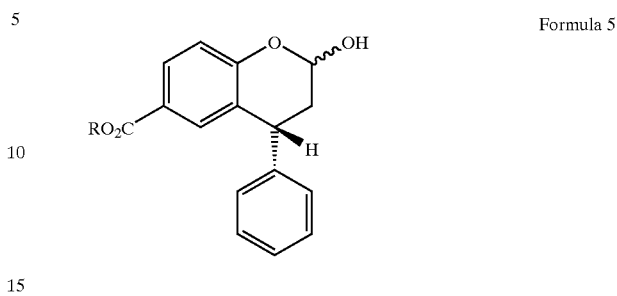

Formula 5

Another aspect of this invention is that, under suitable reaction conditions, the acid lactol of formula 5a is formed from a compound of formula 3 when reduction is carried out with an equivalent excess of hydride reagent.

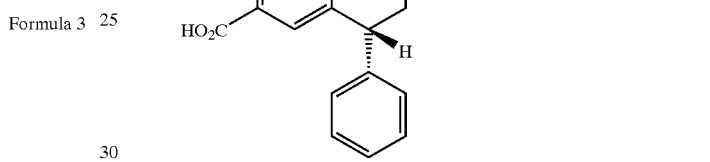

Formula 5a

These lactols of formulae 5 and 5a are suitable substrates for reductive amination with primary, secondary or tertiary amines and lead to compounds of the general formula I. In formula I, R' and R" are the same or different and have the meanings of hydrogen, straight-chained or branched $C_1$–$C_6$ alkyl, preferably methyl or isopropyl. R there has the meaning already mentioned above. The hydrogen gas/precious metal system has proved suitable, preferably palladium. Transfer hydrogenation (ammonium formate/precious metal) or reduction with hydride reagents (e.g. cyanoborohydride) can also be used.

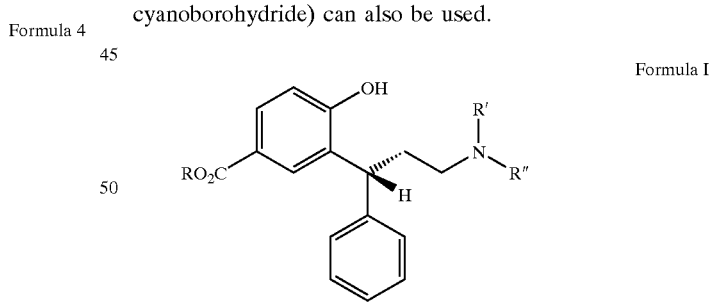

Formula I

Amines of formula I can be obtained both as neutral compounds and as salts, preferably as hydrochlorides, in crystalline form.

Another aspect of the invention is the reduction of the carboxy group of compounds of formula I to hydroxybenzyl alcohols of the structure as reproduced in formula II. Diborane, boron hydride, aluminium hydride, diisobutylaluminium hydride or preferably lithium aluminium hydride are suitable as reducing agents. A compound according to formula II is obtained when R' and R" in formula I each have the meaning of isopropyl.

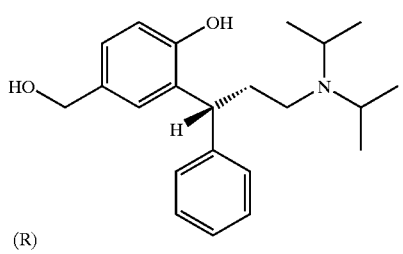

Formula II
(R)

In analogy to the production process mentioned in the document PCT/EP99/03212=WO 99/58478, which was adapted to the present solution to the problem according to the invention, the dextrorotatory enantiomer of a compound of formula II is obtained as a free base. According to the production process for a compound of formula II described with the aid of the following examples, the dextrorotatory enantiomer is obtained. This possesses the R configuration. The hydroxybenzyl alcohol of formula II forms a series of stable, crystalline salts, with hydrochlorides, formates and hydrogen fumarates deserving particular mention.

The hydrogen fumarate salts in particular are highly suitable for the chemically elegant purification of the hydroxybenzyl alcohol.

In particular, the following compounds are produced by the process according to the invention:
- (R,S)-4-phenyl-2-chromanone-6-carboxylic acid
- (R)-4-phenyl-2-chromanone-6-carboxylic acid cinchonidine salt
- (R)-4-phenyl-2-chromanone-6-carboxylic acid
- (R,S)-4-phenyl-2-chromanone-6-carbonyl chloride
- (R)-4-phenyl-2-chromanone-6-carbonyl chloride
- (R,S)-2-oxo-4-phenylchromane-2-carboxylic acid methyl ester
- (R)-2-oxo-4-phenylchromane-2-carboxylic acid methyl ester
- (R,S)-2-oxo-4-phenylchromane-2-carboxylic acid isopropyl ester
- (R)-2-oxo-4-phenylchromane-2-carboxylic acid isopropyl ester
- (4R,4S)-2-(R,S)-hydroxy-4-phenylchromane-6-carboxylic acid methyl ester
- (4R)-2-(R,S)-hydroxy-4-phenylchromane-6-carboxylic acid methyl ester
- (4R,4S)-2-(R,S)-hydroxy-4-phenylchromane-6-carboxylic acid isopropyl ester
- (4R)-2-(R,S)-hydroxy-4-phenylchromane-6-carboxylic acid isopropyl ester
- (4R,4S)-2-(R,S)-hydroxy-4-phenylchromane-6-carboxylic acid
- (4R)-2-(R,S)-hydroxy-4-phenylchromane-6-carboxylic acid
- (R,S)-3-(3-diisopropylamino-1-phenylpropyl)-4-hydroxybenzoic acid methyl ester—base and hydrochloride
- (R)-(−)-3-(3-diisopropylamino-1-phenylpropyl)-4-hydroxybenzoic acid methyl ester—base and hydrochloride
- (R)-(−)-3-(3-diisopropylamino-1-phenylpropyl)-4-hydroxybenzoic acid—base and hydrochloride
- (R,S)-2-(3-diisopropylamino-1-phenylpropyl)-4-hydroxymethylphenol
- (R)-(+)-2-(3-diisopropylamino-1-phenylpropyl)-4-hydroxymethylphenol base, formate and hydrogen fumarate salt The above-mentioned compounds were obtained as illustrated in the overview of Diagram A mentioned below:

Diagram A

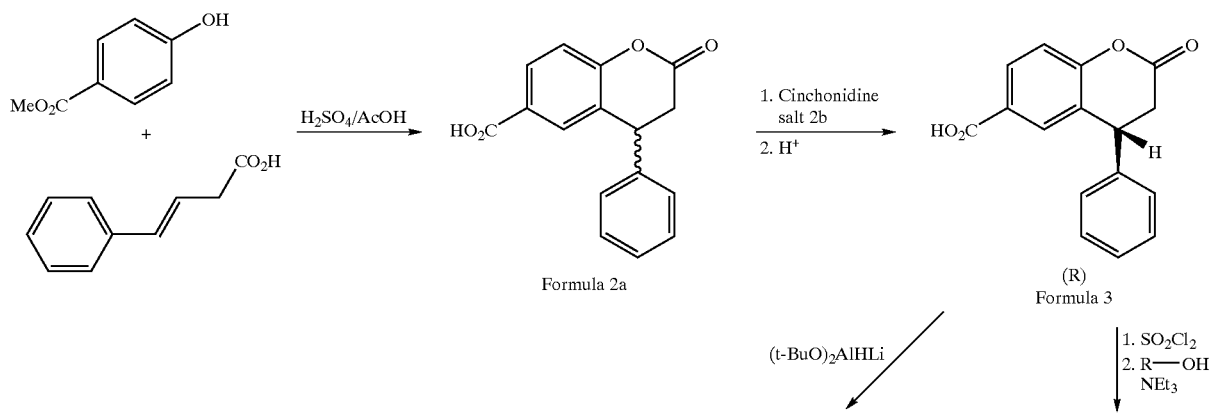

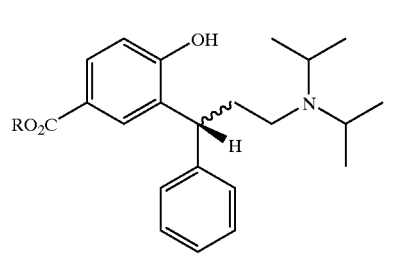

Formula I: R' = R" = i-Pr

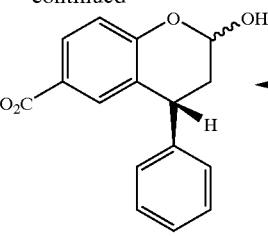

Formula 5a: R = H
Formula 5: R = Me, i-Pr

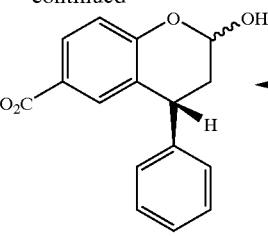

Formula 4

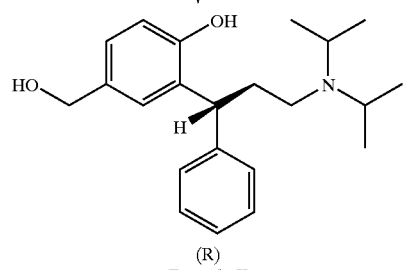

(R)
Formula II

The invention is explained in greater detail with the aid of the following characterisation methods and examples:

I) Characterisation Methods

All the compounds described were completely characterised by $^{1}H$ and/or $^{13}C$ NMR spectroscopy (instrument: Bruker DPX 200). The chemical shifts cited for the $^{13}C$ NMR spectra (50 MHz, ppm values) refer to the solvents $CDCl_3$ (77.10 ppm), $CD_3OD$ (49.00 ppm) or hexadeuteriodimethyl sulfoxide (DMSO-$d_6$, 39.70 ppm). $^{1}H$ NMR data (200 MHz, ppm) are based on internal tetramethylsilane (0.00 ppm).

Determination of the Enantiomeric Purity a) By HPLC:
The separations are performed on a column from Daicel (Chiralpak AD, 250×4.6 mm), the eluent is n-heptane/ethanol/trifluoroacetic acid (92.5/7.5/0.1% v/v), the flow is 1 ml/min, and detection is by UV (250 nm). Typical retention times, e.g. for the enantiomers of (R,S)-1, are 18.0 and 19.5 min.

b) By capillary electrophoresis (CE):
The separations are performed in a Beckman-Coulter model MDQ device in 60 cm (ID: 75 μm) capillaries, with a field of 500 V/cm in a buffer of 100 mM/100 nM tris buffer/boric acid, pH 8.5, in the presence of 3% w/v hydroxypropyl-β-cyclodextrin modifier. The detection is performed using UV at 200 nm. Typical retention times of the enantiomers, e.g. the diacid formed by alkaline hydrolysis of (R,S)-1, are 6.6 and 6.8 minutes.

The optical rotations were determined at 589.3 nm and at ambient temperature using a Perkin Elmer type 241 polarimeter.

The melting points (mp) described are uncorrected and were recorded using a Mettler FP 1 instrument, and in individual cases also by differential thermal analysis (DSC).

IR spectra were recorded on a Perkin-Elmer FTIR 1610 series spectrometer with a resolution of 4 $cm^{-1}$.

Gas chromatographic mass spectroscopy (GC-MS): the spectra (mass/charge ratios and relative intensity (%)) were recorded on a Finnigan TSQ 700 Triple Mass Spectrometer in the positive (P-Cl) or negative (N-Cl) chemical ionisation mode using methane or ammonia as reactant gas. Hydroxyl compounds were analysed as trimethylsilyl ether derivatives. Coupled liquid chromatography-mass spectrometry (LC-MS): Waters Integrity System, Thermabeam Mass Detector (El, 70 eV), mass/charge ratios and relative intensity are reported.

Elemental analyses were prepared by Pascher.

II) EXAMPLES 1. (R,S)-4-Phenyl-2-chromanone-6-carboxylic acid (Formula 2a)

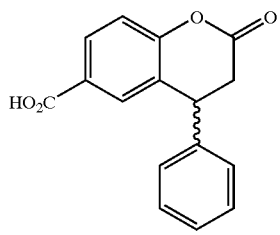

A mixture of cinnamic acid (100 g, 0.68 mol), methyl 4-hydroxybenzoate (108 g, 0.71 mol) and acetic acid (80 ml) is heated to 100° C. 80 ml of 96% sulfuric acid are then added to the resulting clear solution, while stirring. After 2 hours, crystal formation begins. Stirring is continued at the same temperature for 16 hours, the mixture is cooled to ambient temperature and diluted with 500 ml water. The precipitated crystal mass is filtered off, washed with diethyl ether and dried in vacuo.

Crude yield: 142 g (78% of theory), pale beige crystals.
Mp 246° C.

$^{1}$H-NMR (DMSO-$d_6$): 3.18 (d, 2H, J=6.6 Hz, $CH_2$), 4.62 (t, 1H, J=6.6 Hz, CH), 7.14–7.43 (m, 6H), 7.62 (s, 1H), 7.90 (d, 1H, J=8.6 Hz).

$^{13}$C-NMR (DMSO-$d_6$): 35.93, 39.26, 117.20, 126.81, 127.13, 127.65, 127.70, 129.24, 129.95, 130.25, 140.91, 154.80, 166.66, 167.30

Evidence of Structure

Titration with aqueous 0.1 N NaOH in dioxane/water against phenolphthalein gives one equivalent carboxylic acid/mol. In capillary electrophoresis, the electropherogram displays one main peak (>90%) for a singly charged anion. After the alkaline hydrolysis this peak disappeared and a new peak, of equal intensity, appeared with a retention time corresponding to a dianion. An excess of triethylamine is added to a methanolic solution of the acid and this is left at ambient temperature for several days. It is detected by thin layer chromatography that the educt has been converted to a new product. The product displays a methyl ester resonance in the NMR spectra.

Thus, (R,S)-1a is the monobasic acid lactone and not the open-chained phenolic diacid.

2. (R)-4-Phenyl-2-chromanone-6-carboxylic acid cinchonidine salt (Formula 2b)

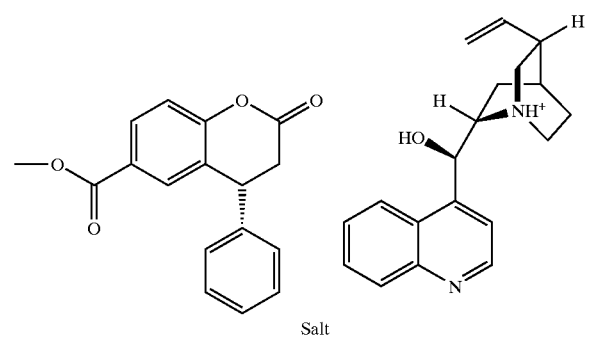

Salt (R/S)-4-Phenyl-2-chromanone-6-carboxylic acid (2.28 g, 8.5 mmol) and 2.36 g (8 mmol) of cinchonidine are dissolved in 40 ml of boiling 2-butanone. This is stirred at ambient temperature for 18 hours and the precipitated crystals are filtered off and dried in vacuo.

Yield: 2.13 g of pale yellow crystals of the cinchonidine salt of (R)-4-phenyl-2-chromanone-6-carboxylic acid (90% of theory, e.e. 90% (HPLC)). Recrystallisation from the same solvent yields a crystalline salt with 99.3% e.e. with a melting point of 197.5° C.

$^{13}$C-NMR (CDCl$_3$/CD$_3$OD): 18.17, 24.39, 26.90, 36.86, 37.21, 40.53, 43.32, 54.12, 60.03, 66.23, 116.51, 118.60, 122.70, 124.73, 127.29, 127.41, 128.07, 129.01, 129.31, 129.78, 130.09, 133.02, 137.70, 140.35, 147.20, 149.57, 153.37, 167.64, 172.87.

$[\alpha]_D^{20}$=−38.7 (c=1.0, MeOH).

3. (R)-4-Phenyl-2-chromanone-6-carboxylic acid (Formula 3)

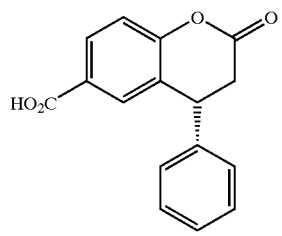

Excess aqueous hydrochloric acid is added to a stirred suspension of the salt 2 in ethyl acetate at ambient temperature. After one hour the organic phase is separated off, washed with water and dried over sodium sulfate. After filtration, it is evaporated to dryness and the crystalline residue is recrystallised from 2-butanone/cyclohexane. Colourless crystals are obtained in an almost quantitative yield (e.e. 99.2%).

Mp 224.9° C.

$^{13}$C-NMR (CDCl$_3$/CD$_3$OD): 36.43, 40.19, 116.92, 125.54, 126.96, 127.10, 127.57, 128.98, 130.29, 130.59, 139.64, 154.71, 167.28, 167.50. $[\alpha]_D^{20}$=+45.7 (c=1.0, MeOH)

4. Carbonyl Chlorides a) (R,S)-4-Phenyl-2-chromanone-6-carbonyl chloride

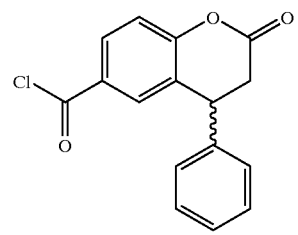

Four drops of pyridine and then 17.7 ml (0.24 mol) of thionyl chloride are added to a mixture of (R/S)-4-phenyl-2-chromanone-6-carboxylic acid (21.5 g, 0.08 mol) in 80 ml of toluene. After stirring for 30 min at ambient temperature, the mixture is heated to 90–100° C. for 2 hours, cooled and evaporated to dryness in a rotary evaporator. The oily residue is taken up in toluene and evaporated again in vacuo. (R/S)-4-phenyl-2-chromanone-6-carbonyl chloride remains as a pale yellow oil in a quantitative yield.

$^1$H-NMR (CDCl$_3$): 3.07 (m, 2H, CH$_2$) 4.41 (t, 1H, J=6.7 Hz, CH), 7.11–7.40 (m, 6H, aryl H), 7.59 (d, 1H, J=2 Hz, aryl H), 8.08 (dd, 1H, J=2/6.5 Hz, aryl H).

$^{13}$C-NMR (CDCl$_3$): 36.43, 40.51, 118.00, 127.34, 128.23, 129.05, 129.49, 129.56, 132.10, 132.69, 139.12, 165.88, 167.03.

b) (R)-4-Phenyl-2-chromanone-6-carbonyl chloride

In the same way, (R)-4-phenyl-2-chromanone-6-carboxylic acid is converted to the compound named in the heading, a pale yellow oil.

5. Carboxylic Acid Esters a) (R,S)-2-Oxo-4-phenylchromane-2-carboxylic acid methyl ester

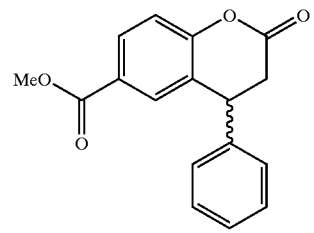

3 g (0.094 mol) of methanol and 16 ml (0.12 mol) of triethylamine in 20 ml of THF are added to a solution of (R/S)-4-phenyl-2-chromanone-6-carboxylic acid chloride (22.9 g, 0.08 mol) in absolute tetrahydrofuran (100 ml) at 0° C., stirring. After stirring for 18 hours at ambient temperature, this is filtered and the filtrate is evaporated to dryness. After recrystallisation from boiling diethyl ester, the residue yields 13.7 g (65% of theory) of (R,S)-2-oxo-4-phenylchromane-2-carboxylic acid methyl ester in the form of colourless crystals.

Mp 97–99° C.

$^{13}$C-NMR (CDCl$_3$): 36.70, 40.55, 52.19, 117.29, 125.78, 126.67, 127.35, 127.88, 129.29, 130.23, 130.54, 139.79, 155.03, 166.00, 166.60.

b) (R)-2-Oxo-4-phenylchromane-2-carboxylic acid methyl ester.

The reaction of (R)-4-phenyl-2-chromanone-6-carboxylic acid chloride as described for the racemate leads to crystalline (R)-2-oxo-4-phenylchromane-2-carboxylic acid methyl ester.

c) (R,S)-2-Oxo-4-phenylchromane-2-carboxylic acid isopropyl ester

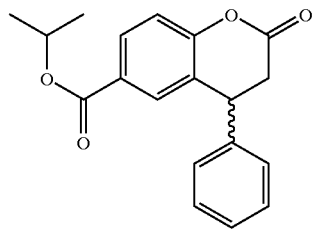

The (R,S)-2-oxo-4-phenylchromane-2-carboxylic acid isopropyl ester is produced in the same way as described for the methyl ester, pale beige crystals, mp 85.9° C.

$^{13}$C-NMR (CDCl$_3$): 21.93, 36.88, 40.65, 68.72, 117.25, 125.58, 127.35, 127.53, 127.91, 129.32, 130.30, 130.51, 139.94, 154.95, 165.09, 166.72.

d) (R)-2-Oxo-4-phenylchromane-2-carboxylic acid isopropyl ester.

(R)-4-Phenyl-2-chromanone-6-carboxylic acid chloride is converted to compounds of formula 4 in the same way.

6. 2-Hydroxy-4-phenylchromane-6-carboxylic acid esters a) (4R,4S)-2-(R,S)-Hydroxy-4-phenylchromane-6-carboxylic acid methyl ester

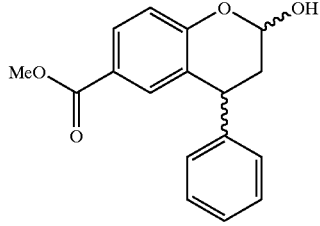

A solution of lithium-tri-tert.-butoxyaluminium hydride (11.6 g, 0.046 mol) in 40 ml of THF is added dropwise to a solution of 11.7 g (0.042 mol) of (R,S)-2-oxo-4-phenylchromane-2-carboxylic acid methyl ester in 60 ml of absolute THF at 0° C., stirring. After two hours the mixture is poured on to 100 ml of water. The aqueous phase is extracted several times with ethyl acetate and the combined organic phases are washed with water, dried over sodium sulfate and evaporated to dryness in vacuo. 11.1 g (95% of theory) of (4R,4S)-2-(R,S)-hydroxy-4-phenylchromane-6-carboxylic acid methyl ester remain as a colourless oil.

$^{13}$C-NMR (CDCl$_3$): Mixture of diastereoisomers (approx. 1:5): 36.15, 36.94, 38.36, 41.05, 51.91, 91.75, 94.81, 117.13, 122.88, 124.95, 125.27, 127.03, 127.24, 128.39, 128.72, 128.88, 129.00, 129.73, 129.93, 131.59, 131.77, 143.13, 143.63, 156.33, 166.98.

b) (4R)-2-(R,S)-Hydroxy-4-phenylchromane-6-carboxylic acid methyl ester (R)-4-Phenyl-2-chromanone-6-carboxylic acid methyl ester is converted to the compound named in the heading in the same way.

c) (4R,4S)-2-(R,S)-Hydroxy-4-phenylchromane-6-carboxylic acid isopropyl ester.

(R,S)-4-Phenyl-2-chromanone-6-carboxylic acid isopropyl ester is converted to the compound named in the heading in the same way.

d) (4R)-2-(R,S)-Hydroxy-4-phenylchromane-6-carboxylic acid isopropyl ester.

(R)-4-Phenyl-2-chromanone-6-carboxylic acid isopropyl ester is converted to the compound named in the heading in the same way.

7. 2-Hydroxy-4-phenylchromane-6-carboxylic acids a) (4R,4S)-2-(R,S)-Hydroxy-4-phenylchromane-6-carboxylic acid

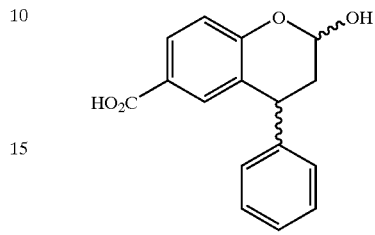

(R,S)-4-Phenyl-2-chromanone-6-carboxylic acid is converted to the compound named in the heading in the same way.

b) (4R)-2-(R,S)-Hydroxy-4-phenylchromane-6-carboxylic acid

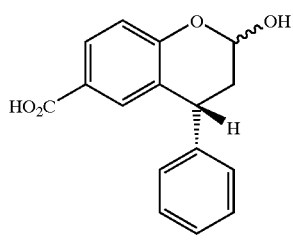

(R)-4-Phenyl-2-chromanone-6-carboxylic acid is converted to the compound named in the heading in the same way.

8. 3-(3-Diisopropylamino-1-phenylpropyl)-4-hydroxybenzoic acid methyl ester a) (R,S)-3-(3-Diisopropylamino-1-phenylpropyl)-4-hydroxybenzoic acid methyl ester—base and hydrochloride

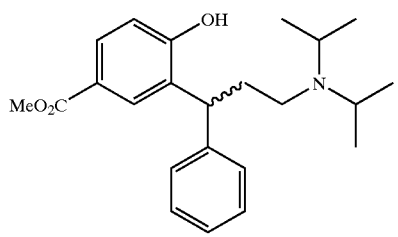

0.4 g of palladium carbon catalyst (10% Pd) are added to a solution of 11.1 g (0.039 mol) of (4R,4S)-2-(R,S)-hydroxy-4-phenylchromane-6-carboxylic acid methyl ester and 21 ml (0.15 mol) of diisopropylamine in 100 ml of methanol and hydrogenated at ambient temperature under a pressure of 4 bar. After flushing the apparatus with nitrogen gas, the mixture is filtered and the filtrate evaporated to dryness and taken up in diethyl ether. The clear, colourless solution is cooled to 5° C. and a light stream of dry hydrogen chloride gas is passed through. The precipitated colourless crystals of (R,S)-3-(3-diisopropylamino-1-phenylpropyl)-4-hydroxybenzoic acid methyl ester hydrochloride are filtered off and dried in vacuo (10.9 g, 69% of theory).

Mp 116.4° C.

$^{13}$C-NMR (DMSO-d$_6$): 16.51, 18.11, 18.78, 31.53, 41.30, 45.81, 51.83, 54.14, 115.60, 120.43, 126.62, 128.01, 128.61, 129.25, 129.53, 130.01, 143.04, 159.77, 166.30.

The free base is obtained by stirring an ethyl acetate suspension of the hydrochloride with excess aqueous sodium carbonate solution. The organic phase is washed with water, dried over sodium sulfate, filtered and evaporated to dryness (quantitative yield).

b) (R)-(−)-3-(3-Diisopropylamino-1-phenylpropyl)-4-hydroxybenzoic acid methyl ester

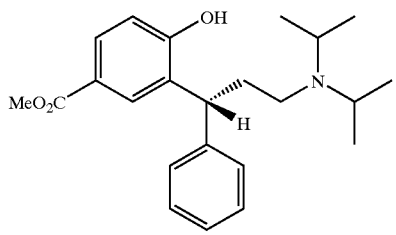

In the same way as described for the racemate, the optically active (R)-(−)-3-(3-diisopropylamino-1-phenylpropyl)-4-hydroxybenzoic acid methyl ester is produced from (4R)-2-(R,S)-hydroxy-4-phenylchromane-6-carboxylic acid methyl ester in 99.6% purity (HPLC).

Mp: 143.7° C. (DSC: 144.7° C.)

$[\alpha]_D^{20}$=−26.6 (c=0.93, EtOH).

$^{13}$C-NMR (CDCl$_3$): 18.74, 19.62, 33.12, 39.68, 42.36, 48.64, 51.42, 117.99, 120.32, 126.23, 128.30, 128.85, 129.39, 130.26, 132.21, 144.06, 162.43, 167.35.

MS (EI, 70 eV): 369 (M$^+$, 3%), 354 (13%), 265 (3%), 237 (5%), 209 (5%), 209 (5%), 181 (5%), 152 (4%), 126 (8%), 114 (100%).

9. (R)-(−)-3-(Diisopropylamino-1-phenylpropyl)-4-hydroxybenzoic acid

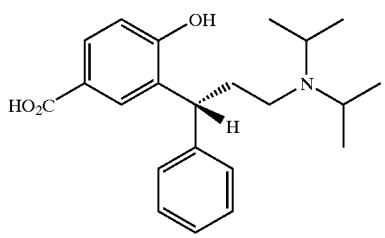

Produced from (4R)-2-(R,S)-hydroxy-4-phenylchromane-6-carboxylic acid as described above.

Hydrochloride

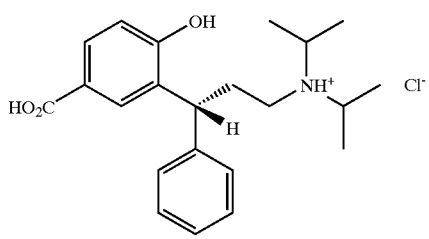

Produced from the base (R)-(−)-3-(3-diisopropylamino-1-phenylpropyl)-4-hydroxybenzoic acid and HCl gas in ethyl acetate, recrystallisation from boiling water.

Mp: 260.7° C.

$[\alpha]_D^{20}$ =−28.8 (c=1, MeOH)

$^{13}$C-NMR (DMSO-d$_6$): 16.57, 18.12, 31.68, 41.26, 45.89, 54.19, 115.43, 121.59, 124.99, 126.63, 128.09, 128.65, 129.47, 129.83, 143.17, 159.41, 167.44.

Calculated for C$_{22}$H$_{30}$ClNO$_3$ (mol. wt. 391.94): C 67.42%, H 7.72%, Cl 9.05%, N 3.57%, O 12.25%; experimental values: C 65.63%, H 7.68%, Cl 8.54%, N 3.68%, O 12.05%.

10. (R,S)-2-(3-Diisopropylamino-1-phenylpropyl)-4-hydroxymethylphenol

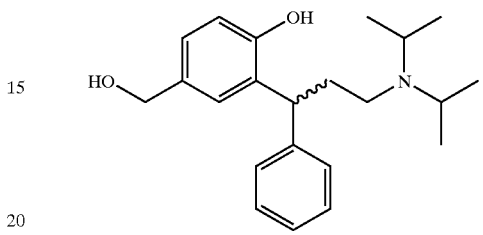

A solution of 9.1 g (24.6 mmol) of (R,S)-3-(3-diisopropylamino-1-phenylpropyl)-4-hydroxybenzoic acid methyl ester in 50 ml of THF is slowly added dropwise at 0° C. to a suspension of lithium aluminium hydride (0.94 g, 24.7 mmol), with stirring. After stirring for two hours, this is heated to ambient temperature and stirred for a further two hours. The mixture is cooled down (0° C.) and 1 ml of water and 1 ml of 10% aqueous sodium hydrogencarbonate solution are added dropwise, consecutively. After filtering, and washing the filtration residue with THF, the combined organic phases are evaporated to dryness. The remaining viscous, pale yellow oil (7.8 g) is taken up in ethyl acetate and the solution is washed with 10% aqueous sodium hydrogencarbonate solution. After drying (sodium sulfate), filtering and evaporating, the residue is recrystallised from a small amount of ethyl acetate. After drying in vacuo, 5 g (59% of theory) of (R,S)-2-(3-diisopropylamino-1-phenylpropyl)-4-hydroxymethylphenol are obtained in the form of pale beige crystals.

Mp 112.2° C.

$^{13}$C-NMR (CDCl$_3$): 19.57, 19.95, 33.34, 39.55, 42.13, 48.01, 65.34, 118.50, 126.27, 126.54, 127.50, 128.37, 128.54, 132.61, 132.77, 144.56, 155.46.

11. (R)-(+)-2-(3-Diisopropylamino-1-phenylpropyl)-4-hydroxymethylphenol (Formula II)

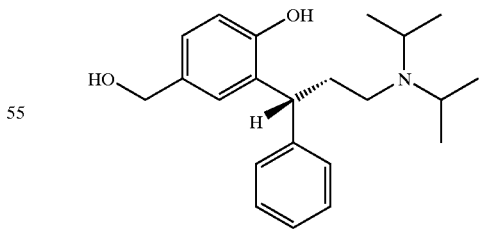

Produced from (R)-(−)-3-(diisopropylamino-1-phenylpropyl)-4-hydroxybenzoic acid methyl ester as described above.

Colourless crystals, mp 102.3° C. (from ethyl acetate).

$[\alpha]_D^{22}$=+21.3 (c=1.0, EtOH).

12. Formate Salt

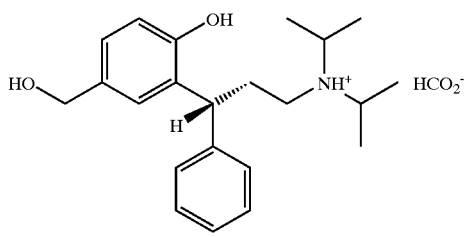

138.1 mg (3.0 mmol) of formic acid are added to a solution of (R)-2-(3-diisopropylamino-1-phenylpropyl)-4-hydroxymethylphenol (1.02 g, 3.0 mmol) in 7.5 g of acetonitrile at ambient temperature. The oil that is precipitated is brought into solution by heating. Standing overnight leads to the formation of coarse, colourless crystals, which are sucked off and dried (yield: almost quantitative), purity (HPLC): 97.7%.

Mp: 151.8° C.

$[\alpha]_D^{20} = -7.3$ (c=1, water)

$^{13}$C-NMR (DMSO-$d_6$): 19.16, 19.27, 34.21, 41.06, 44.46, 50.78, 63.16, 114.96, 125.72, 126.00, 126.31, 128.08, 128.30, 130.14, 132.96, 144.73, 153.74, 164.98.

13. Hydrogen Fumarate Salt

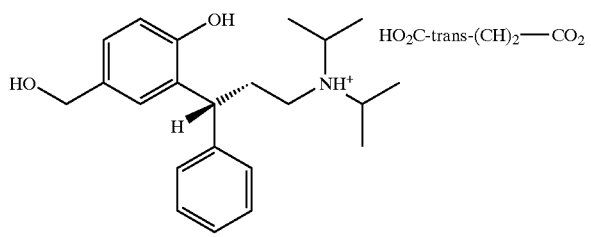

Formula 6

A solution of 1.0 g (8.61 mmol) of fumaric acid in 100 ml of acetone is added to a solution of (R)-2-(3-diisopropylamino-1-phenylpropyl)-4-hydroxymethylphenol (2.94 g, 8.61 mmol) in 25 ml of acetone at ambient temperature. The colourless, crystalline salt that spontaneously precipitates is stirred for a further 30 minutes at ambient temperature, sucked off and dried in vacuo.

Yield: 3.94 g (100% of theory).

Mp 216.1° C.

Solubilities at ambient temperature (mg/ml): <0.2 in ethyl acetate, 2-butanone, dichloromethane; >50 in methanol; approx. 10 in water.

$^{13}$C-NMR (CD$_3$OD): 17.97, 33.68, 43.19, 47.72, 56.31, 65.05, 116.29, 127.58, 128.04, 128.46, 129.13, 129.53, 130.55, 133.73, 136.29, 144.37, 155.41, 171.38.

What is claimed is:

1. A process for the production of 3,3-diarylpropylamines of the general formula I

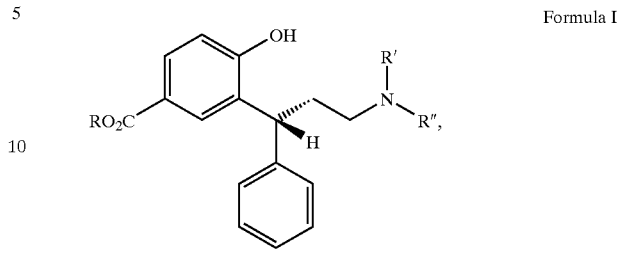

Formula I wherein

R is selected from the group consisting of hydrogen, straight-chained and branched $C_1$–$C_8$ alkyl, R' and R" can be the same or different and are selected from the group consisting of straight-chained and branched $C_1$–$C_6$ alkyl, the process comprising condensing a compound of general formula 1

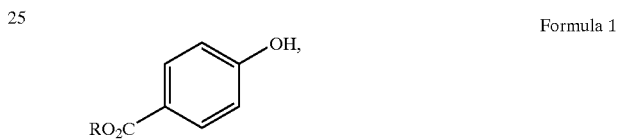

Formula 1 wherein R is defined as above, with cinnamic acid to form a compound of the general formula 2a

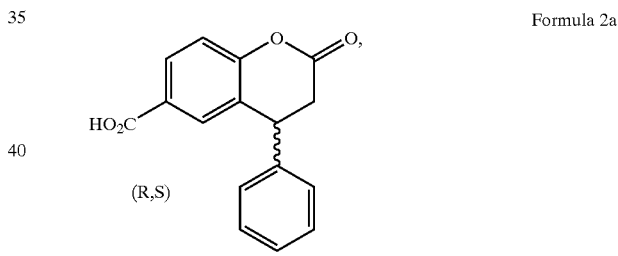

Formula 2a then reacting the compound of general formula 2a with a tertiary chiral amine to form a compound of the general formula 2b

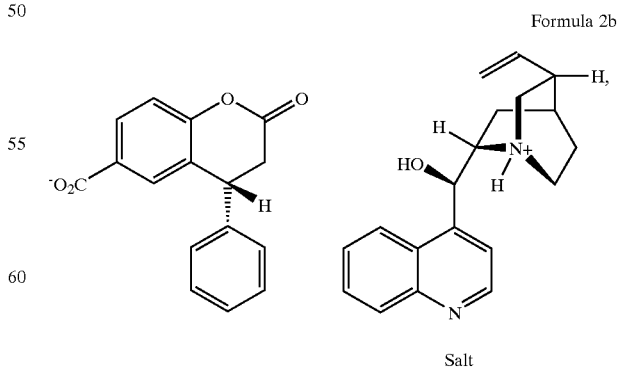

Formula 2b

Salt subsequently, treating the compound of the general formula 2b by acidification to isolate a compound of formula 3

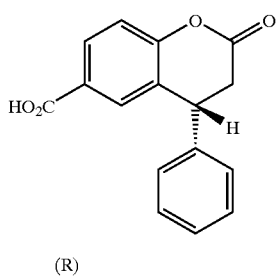

Formula 3

(R)

in crystalline form, which is converted, via an intermediate step of an acid chloride, with continuing ester formation with alcohols of the formula R—OH, wherein R is defined as above, to a compound of the general formula 4

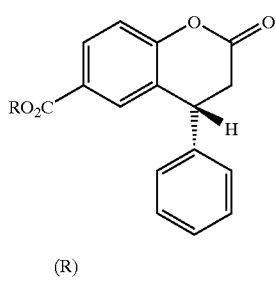

Formula 4

(R)

and, in a further reaction step, hydrogenating the compound of the general formula 4 using diisobutylaluminium hydride or lithium tri-tert.-butoxyaluminium hydride, to lactols of general formula 5

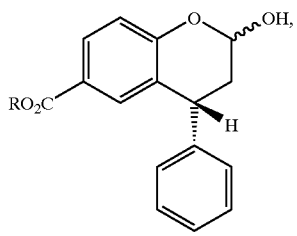

Formula 5 and reductively aminating the compound of general formula 5 with primary, secondary or tertiary amines to form compounds of the general formula I

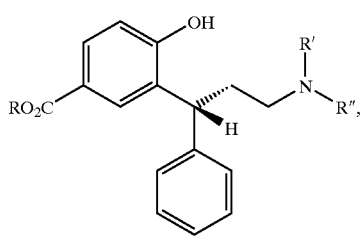

Formula 1 wherein R, R' and R" are defined as above.

2. The process according to claim 1, wherein the compound of formula 3 is converted to the compound of formula 4 using thionyl chloride or oxalyl chloride with the formation of the intermediate step of an acid chloride with alcohols of the formula R—OH, wherein R is defined as in claim 1.

3. The process according to claim 1, wherein the compound of formula 3 is directly reduced to a compound of formula 5a using an equivalent excess of hydride reagent.

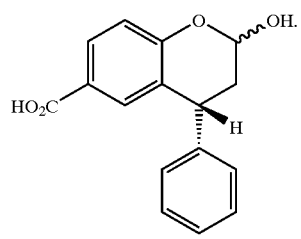

Formula 5a

4. The process according to claims 1 to 3, wherein a compound of formula I, wherein R' and R" are isopropyl, is reduced on its carboxy group to obtain a compound of formula II.

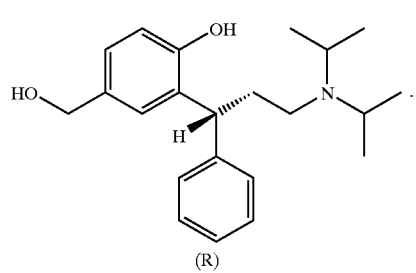

Formula II (R)

5. A compound corresponding to general formula 2a.

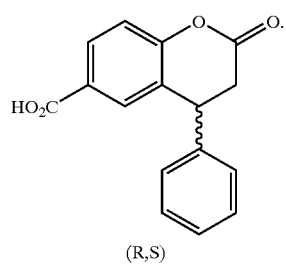

Formula 2a (R,S)

6. A compound corresponding to general formula 2b.

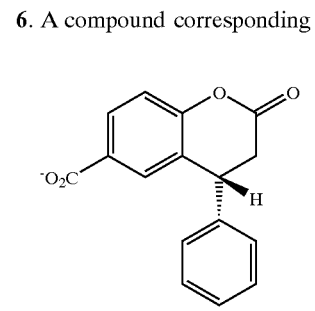

Formula 2b

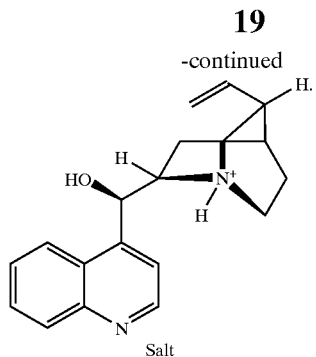

Salt

7. A compound corresponding to formula 3.

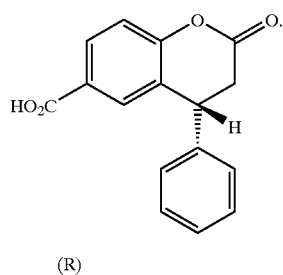

Formula 3

(R)

8. A method of producing a dextrorotatory hydroxybenzyl alcohol of formula II comprising reacting the compound of formula 2a with a tertiary chiral amine to form a compound of the general formula 2b

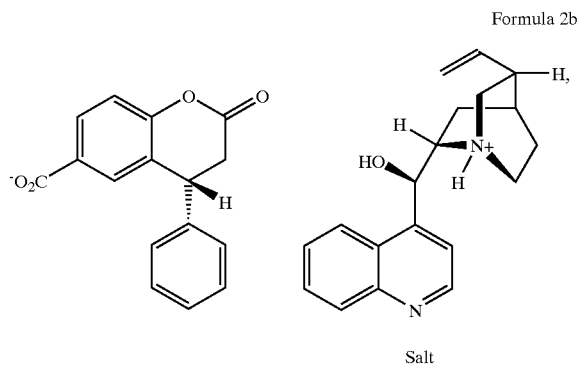

Formula 2b

Salt subsequently, treating the compound of the general formula 2b by acidification to isolate a compound of the general formula 3

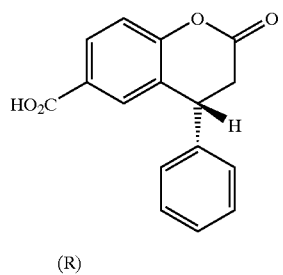

Formula 3

(R)

in crystalline form, which is converted, via an intermediate step of an acid chloride, with continuing ester formation with alcohols of the formula R—OH, wherein R is defined as in claim 1, to a compound of the general formula 4

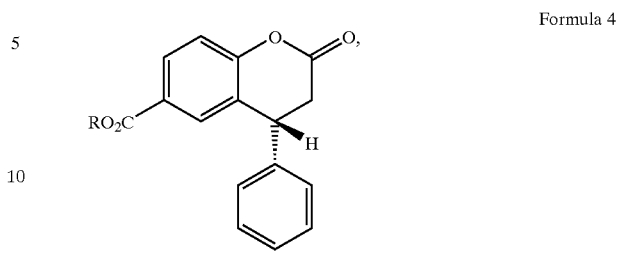

Formula 4

(R)

hydrogenating the compound of the general formula 4 using diisobutylaluminium hydride or lithium tri-tert.-butoxyaluminium hydride, to lactols of the general formula 5,

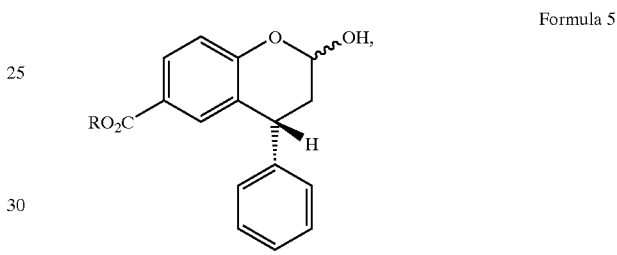

Formula 5 reductively aminating the compound of the general formula 5 with primary, secondary or tertiary amines to form compounds of the general formula I,

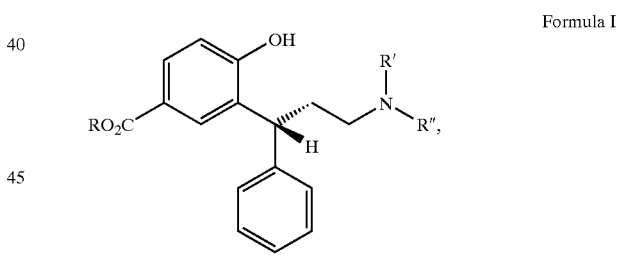

Formula I wherein R' and R" are isopropyl, and reducing the compounds of Formula I on their carboxy groups to obtain the compound of Formula II.

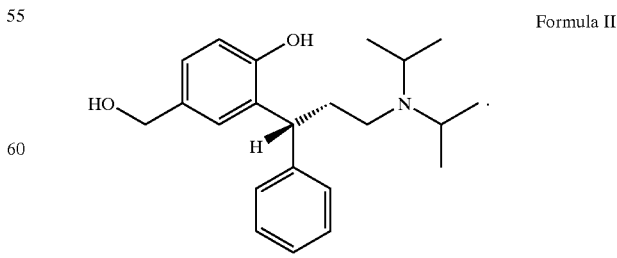

Formula II (R)

9. A compound corresponding to formula 6.

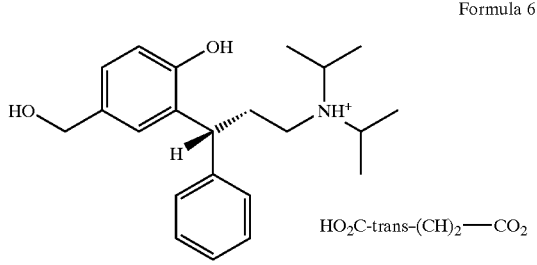

Formula 6

HO₂C-trans-(CH)₂—CO₂

10. A method of manufacturing a pharmaceutical composition for the treatment of incontinence comprising providing the compound of claim 9 and formulating said compound with pharmaceutically acceptable adjuvants to obtain the pharmaceutical composition.

11. The process of claim 1 wherein R is methyl or isopropyl.

12. The process of claim 1 wherein R' and R" are methyl or isopropyl.

13. A method of producing a dextrorotatory hydroxybenzyl alcohol of formula II comprising reacting the compound of formula 2b Formula 2b Salt by acidification to isolate a compound of general formula 3

Formula 3

(R)

in crystalline form, which is converted, via an intermediate step of an acid chloride, with continuing ester formation with alcohols of the formula R—OH, wherein R is defined as in claim 1, to a compound of the general formula 4, Formula 4

(R)

hydrogenating the compound of the general formula 4 using diisobutylaluminium hydride or lithium tri-tert.-butoxyaluminium hydride, to lactols of the general formula 5, Formula 5 reductively aminating the compound of the general formula 5 with primary, secondary or tertiary amines to form compounds of the general formula I, Formula I wherein R' and R" are isopropyl, and reducing the compounds of Formula I on their carboxy groups to obtain the compound of Formula II Formula II (R)

14. A method of producing dextrorotatory hydroxybenzyl alcohol of formula II comprising converting a crystalline form of a compound of general formula 3, Formula 3

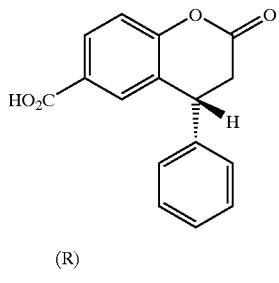

(R)

via an intermediate step of an acid chloride, with continuing ester formation with alcohols of the formula R—OH, wherein R is defined as in claim 1, to a compound of the general formula 4, Formula 4

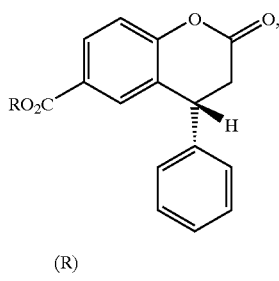

(R)

hydrogenating the compound of the general formula 4 using diisobutylaluminium hydride or lithium tri-tert.-butoxyaluminium hydride, to lactols of the general formula 5, Formula 5

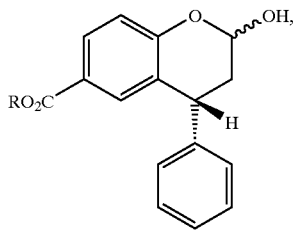

reductively aminating the compound of the general formula 5 with primary, secondary or tertiary amines to form compounds of the general formula I, Formula I

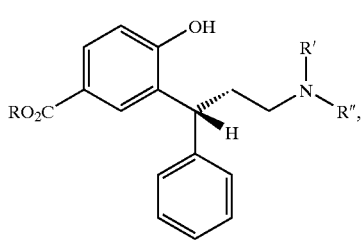

wherein R' and R" are isopropyl, and reducing the compounds of Formula I on their carboxy groups to obtain the compound of Formula II.

Formula II

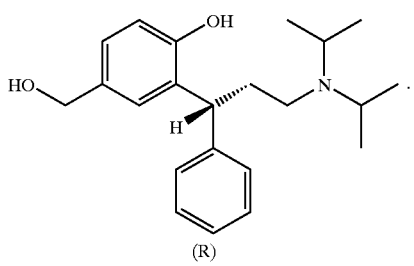

(R)

* * * * *

UNITED STATES PATENT AND TRADEMARK OFFICE
CERTIFICATE OF CORRECTION

PATENT NO. : 6,809,214 B2
DATED : October 26, 2004
INVENTOR(S) : C. O. Meese

It is certified that error appears in the above-identified patent and that said Letters Patent is hereby corrected as shown below:

Title page,
Item [73], Assignee, please correct "Schwartz Pharma AG" to
-- Schwarz Pharma AG --.

Column 1,
Line 11, please add the following paragraph:
-- The invention relates to a process for the production of derivatives of 3,3-diarylpropylamines of the general formula I and of sterically highly pure, stable intermediates, and to their use for the production of pharmaceutical compositions. --.

Signed and Sealed this

Sixteenth Day of August, 2005

JON W. DUDAS
*Director of the United States Patent and Trademark Office*